(12) United States Patent
Mulcaire-Jones (10) Patent No.: US 7,588,544 B2
(45) Date of Patent: Sep. 15, 2009

(54) APPARATUS AND METHOD OF FERTILITY AWARENESS

(75) Inventor: George Mulcaire-Jones, Butte, MT (US)

(73) Assignee: Maternal Life International, Butte, MT (US)

( * ) Notice: Subject to any disclaimer, the term of this patent is extended or adjusted under 35 U.S.C. 154(b) by 166 days.

(21) Appl. No.: 10/783,647

(22) Filed: Feb. 20, 2004

(65) Prior Publication Data
US 2004/0167424 A1   Aug. 26, 2004

Related U.S. Application Data

(60) Provisional application No. 60/448,677, filed on Feb. 20, 2003.

(51) Int. Cl.
*A61B 10/00* (2006.01)
(52) U.S. Cl. .................................. 600/551
(58) Field of Classification Search .............. 600/551
See application file for complete search history.

(56) References Cited

U.S. PATENT DOCUMENTS

| | | | | |
|---|---|---|---|---|
| 1,661,877 | A * | 3/1928 | Costello | 235/123 |
| 3,964,674 | A | 6/1976 | Van der Gaast | 235/88 |
| 5,903,524 | A | 5/1999 | Clarke | 368/240 |
| 6,585,663 | B1 | 7/2003 | Coley et al. | 600/551 |
| 6,747,917 | B2 * | 6/2004 | Jennings et al. | 368/10 |

OTHER PUBLICATIONS

Marcus, Amy Dockser. "The Rhythm Method Gets an Update." Wall Street Journal. Dec. 9, 2003.

"Fertility Awareness." Family Health International. Network. vol. 17 No. 1, Fall 1996. pp. 1-24.

Queenan et al. "Natural Family Planning: Current Knowledge and New Strategies for the 1990s". American Journal of Obstetrics and Gynecology. pp. 1A-8A (1991).

Wilcox, Allen J. et al. "Timing of Sexual Intercourse in Relation to Ovulation" The New England Journal of Medicine. vol. 333, No. 23, Dec. 7, 1995. pp. 1517-1521.

Stanford et al. "Interest in Natural Family Planning Among Female Family Practice Patients." Family Practice Research Journal, vol. 14, No. 3, 1994 pp. 237-249.

Arevalo et al. "A Fixed Formula to Define the Fertile Window of the Menstrual Cycle as the Basis of a Simple Method of Natural Family Planning." Original Research Article. pp. 357-360. (1999).

Professional Information. ClearPlan Easy Fertility Monitor. Unipath. (2000).

Kippley et al. "The Art of Natural Family Planning". The Couple to Couple League International, Inc. (CCL). NFP Rules: Phase I. Fourth Edition. pp. 108-110. (No date).

(Continued)

*Primary Examiner*—Jeffrey G. Hoekstra
(74) *Attorney, Agent, or Firm*—Marsh Fischmann & Breyfogle LLP (57) ABSTRACT

A method of providing visual indications relating to various phases of a woman's menstrual cycle and an apparatus for providing visual indications relating to various phases of a woman's menstrual cycle are provided. As many as ten different types of beads are utilized in the method and apparatus of the present invention to provide the desired visual indications. Different beads are placed on a string each day during the woman's menstrual cycle depending upon the phase of the woman's menstrual cycle and other events observed during such phases.

18 Claims, 3 Drawing Sheets

OTHER PUBLICATIONS

Stanford et al. "Timing Intercourse to Achieve Pregnancy: Current Evidence." Health Research Center, Department of Family and Preventive Medicine, and Division of Reproductive Endocrinology and Infertility. vol. 100, No. 6, Dec. 2002 pp. 1333-1341.

Fehring, Richard J. "Methods Used to Self-Predict Ovulation: A Comparative Study." Clinical Studies. 19:3 May/Jun. 1990.

Hilgers et al. "Natural Family Planning: *I. The Peak Symptoms and Estimated Time of Ovulation.*" The American College of Obstetricians and Gynecologists. vol. 52, No. 5 Nov. 1978.

* cited by examiner

APPARATUS AND METHOD OF FERTILITY AWARENESS

RELATED APPLICATION INFORMATION

This application claims priority from U.S. Provisional Application Ser. No. 60/448,677 entitled "APPARATUS AND METHOD OF FERTILITY AWARENESS" filed on Feb. 20, 2003, the entire disclosure of which is hereby incorporated herein.

FIELD OF THE INVENTION

The present invention relates generally to natural family planning methods, and more particularly to providing visual indications relating to various phases of a woman's menstrual cycle.

BACKGROUND OF THE INVENTION

A normal woman's menstrual cycle has three general phases, namely, 1) a phase when the woman experiences menstrual bleeding; 2) a phase when a woman discharges cervical mucus and ovulates; and 3) a phase when the ovulated egg has died and the cervical mucus has dried up. In phase 1 (the menses phase), the woman is in a phase of unlikely fertility. When the woman is in phase 2 (the fertile phase), the woman is in a phase of possible fertility. When the woman is in phase 3 (the infertile phase), the woman is in a phase of complete infertility.

There are a number of natural family planning systems that have been developed and are being used successfully by women and couples. However, there are limitations methodologically and educationally to each of these systems. Despite the availability of existing natural family planning systems, only 2 percent of couples in the United States and 5 percent world wide use natural means of birth regulation. In this context, there is a need for more "user friendly" systems that reflect current scientific evidence in regard to natural family planning and present the continuum of natural family planning use.

Existing sympto-thermal systems integrate mucus observations with post-ovulatory temperature changes. However, recent studies suggest that the correlation of biphasic temperature changes to ovulation is accurate in only 70 percent of cases. Sympto-thermal methods are also dependent upon written literacy in which women are able to comfortably read a thermometer, chart temperatures and interpret the temperature pattern. This level of written literacy may be difficult to achieve in many areas of the world, effectively precluding sympto-thermal NFP system use.

Existing ovulation methods rely solely on mucus observations and interpretations. In this way, they can be accessible to both literate and non-literate users. However existing mucus only methods are based upon data that may not accurately reflect day specific pregnancy probabilities. By recommending abstinence during vaginal bleeding and emphasizing the use of "dry days" before ovulation, such methods may increase surprise pregnancy rates. Such pre-ovulatory surprise pregnancy rates have been documented in the World Health Organization data that examined ovulation method effectiveness.

A recently developed method of natural family planning (The Standard Days Method) holds promise as a simplified method of fertility awareness. While the method relies on day-specific pregnancy probabilities, it is limited to use in women with regular cycles from 26 to 32 days.

Finally, there is a need to make natural family planning relevant culturally and generationally. Within the United States and Europe, there is interest in natural, non-hormonal and non-invasive means of medical and reproductive health care. At the same time, women and couples of reproductive age, have grown up accustomed to technological interventions and instrumentations as a part of every day life. Meanwhile, in the developing world, women and couples may have a wide range of educational backgrounds. For example, in Africa as a whole, only 40 percent of women are considered literate. In the context of widespread illiteracy, there is a need for family planning systems that are simple, visual and can be used by all women and couples, regardless of their educational background.

SUMMARY OF THE INVENTION

Accordingly, the present invention provides a method and apparatus for tracking the menses phase, the fertility phase and the infertile phase during a woman's menstrual cycle. This method and apparatus are used to indicate when a woman may be more likely to become pregnant. Thus, this method and apparatus can be used when a woman wants to become pregnant and also by a woman who wants to avoid pregnancy.

The method of the present invention generally involves stringing different types of beads on a string to visually indicate the phase in which the woman is in during her menstrual cycle. Different types of beads are provided for each of the three phases. In a preferred embodiment, red beads are used to indicate the menses phase, green beads are used to indicate the fertile phase and yellow beads are used to indicate the infertile phase.

In accordance with the present invention, a woman starts stringing a red colored bead at the beginning of her menses phase, shifts to a green colored bead when in the fertile phase, and shifts to a yellow bead when in the infertile phase. A woman seeking to become pregnant would try to have intercourse when in the fertile phase, and thus when the green beads associated with this phase are being strung on the string. On the other hand, a woman seeking not to become pregnant would have intercourse preferably during the infertile phase when yellow beads are being used and when the ovulated egg has died and cervical mucus has dried up.

The present invention is used by a woman to visually indicate what phase the woman is in during her menstrual cycle. As stated above, the first red bead is placed on the string when the woman has begun her menses. Successive red beads are then placed on the string, one for each successive day, until there is a cross-over to the fertile phase during which the woman discharges cervical mucus and ovulates. At this point, a cross-over bead is strung on the string. The cross-over point is typically determined by the woman's knowledge of her own fertility cycle. For example, the cross-over bead is typically placed on the string anywhere from three red beads to six red beads into the menstrual cycle, depending on the woman's knowledge of her own menstrual cycle. Once the fertile phase is entered, then a green bead is placed on the string to indicate the woman is in the fertile phase. The number of days in this phase are indicated by placing beads on the string, one for each day. During this period, the woman observes her cervical mucus. If the mucus is clear, not white or yellow, and is slippery and wet when touched, then the woman is in phase two, the fertile phase.

It is also contemplated that during the fertile phase that the woman might use an ovulation prediction kit which detects a hormone called luteinizing hormone (LH). It is known that when the level of LH measured in a woman's blood peaks, ovulation occurs within 24-36 hours after this peak. Urine based ovulation prediction kits are available which detect a critical value of LH in a woman's urine. It is well-known that the LH surge is detectible in her urine approximately four to six hours after the LH peaks in her blood. A special bead is placed on the string indicating when the LH surges. This serves as a guide to help a woman and couple identify when ovulation will occur. The ovulation kit is used generally when a woman wants to become pregnant. It also assists a couple in learning the method by giving them an additional sign that they are in the possibly fertile phase of the menstrual cycle.

At some point during the woman's menstrual cycle, the cervical mucus will begin to "dry up," becoming stickier, less viscous and less clear. A special type of bead—the "Drying Up Bead"—is placed on the string on the first day the cervical mucus changes from egg white and begins to dry up. This is followed by additional drying up beads (typically three)—one for each day that cervical mucus is drying up. Next, another special type of bead, which in one embodiment is a "yellow diamond" bead, is placed on the string to indicate the beginning of the infertile phase. Thereafter, yellow color beads are then placed on the string to indicate the woman is in the infertile phase. This continues until the menses phase begins, at which point the process is repeated.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following Detailed Description, taken in conjunction with the drawings, in which.

DETAILED DESCRIPTION

Figure 1A:
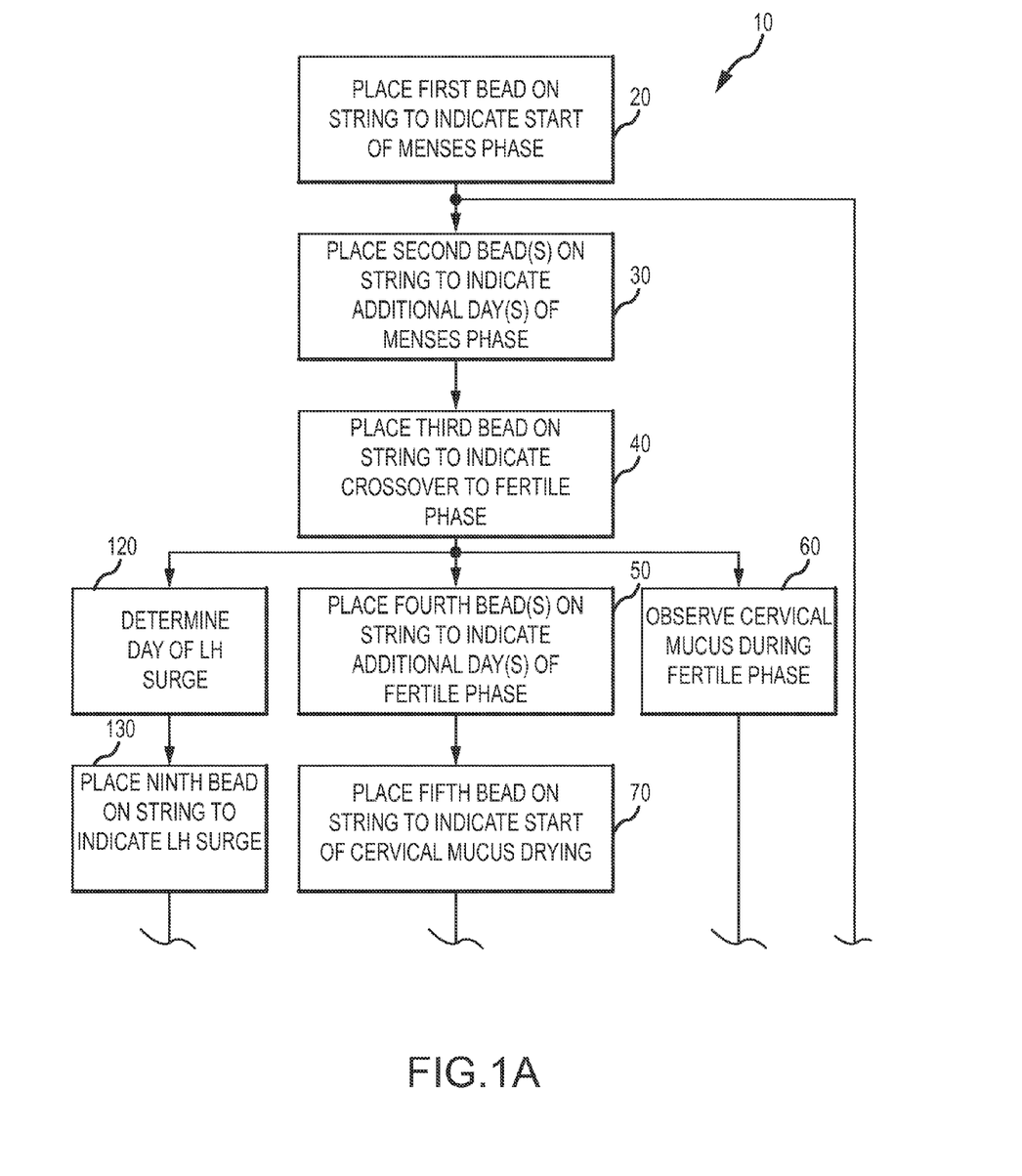
FIGS. 1A-B are a flowchart showing the steps involved in one embodiment of a method of providing visual indications relating to various phases of a woman's menstrual cycle in accordance with the present invention.
Figure 1B:
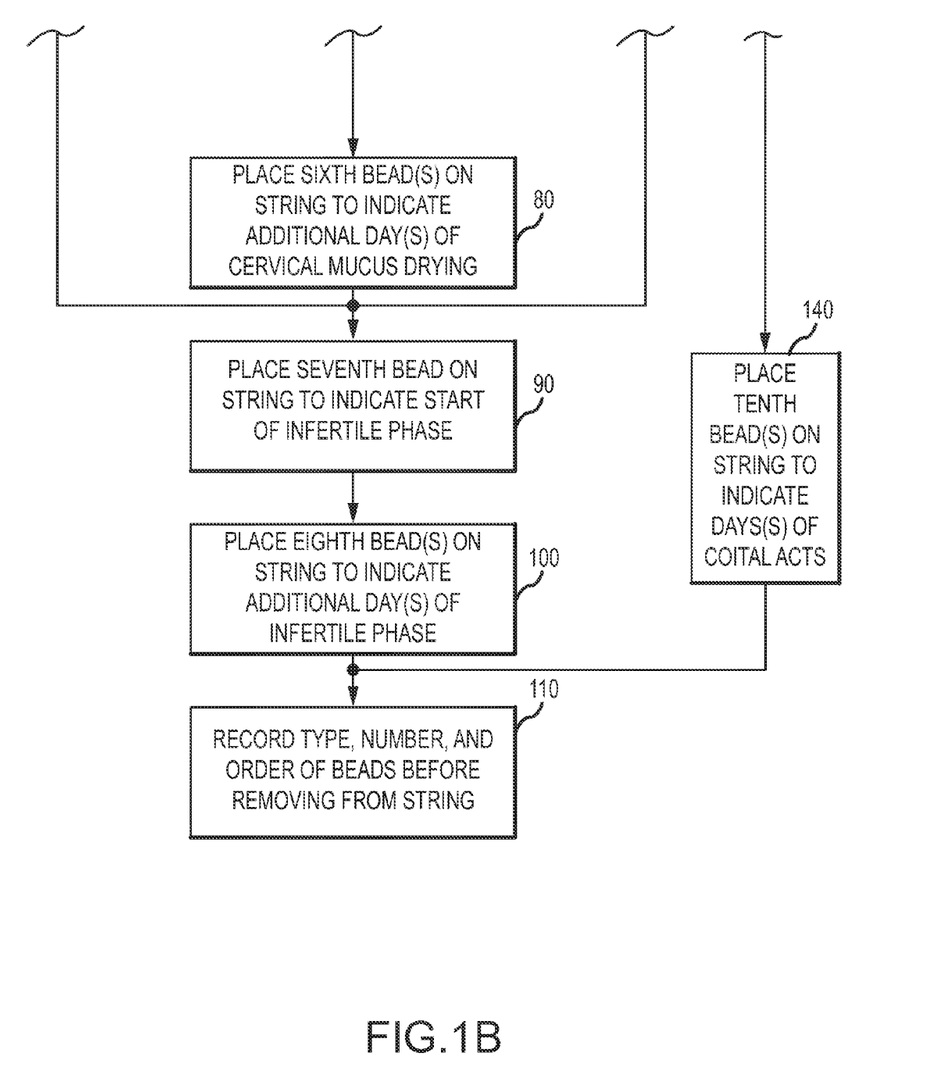

FIGS. 1A-1B show the steps involved in one embodiment of a method (10) of providing visual indications relating to various phases of a woman's menstrual cycle. In general, the method (10) involves placing a bead on a string during each day of the woman's menstrual cycle. Different types of beads are utilized to provide indications of the three different phases (i.e., menses, fertile and infertile phase) as well as various significant events during the three phases. The method (10) may be undertaken by a woman on her own or in conjunction with another (e.g., her spouse) to monitor her menstrual cycle in order to assess the best days to engage in sexual intercourse if she wants to become pregnant or to avoid sexual intercourse during certain days if she wants to avoid becoming pregnant.

Figure 2:
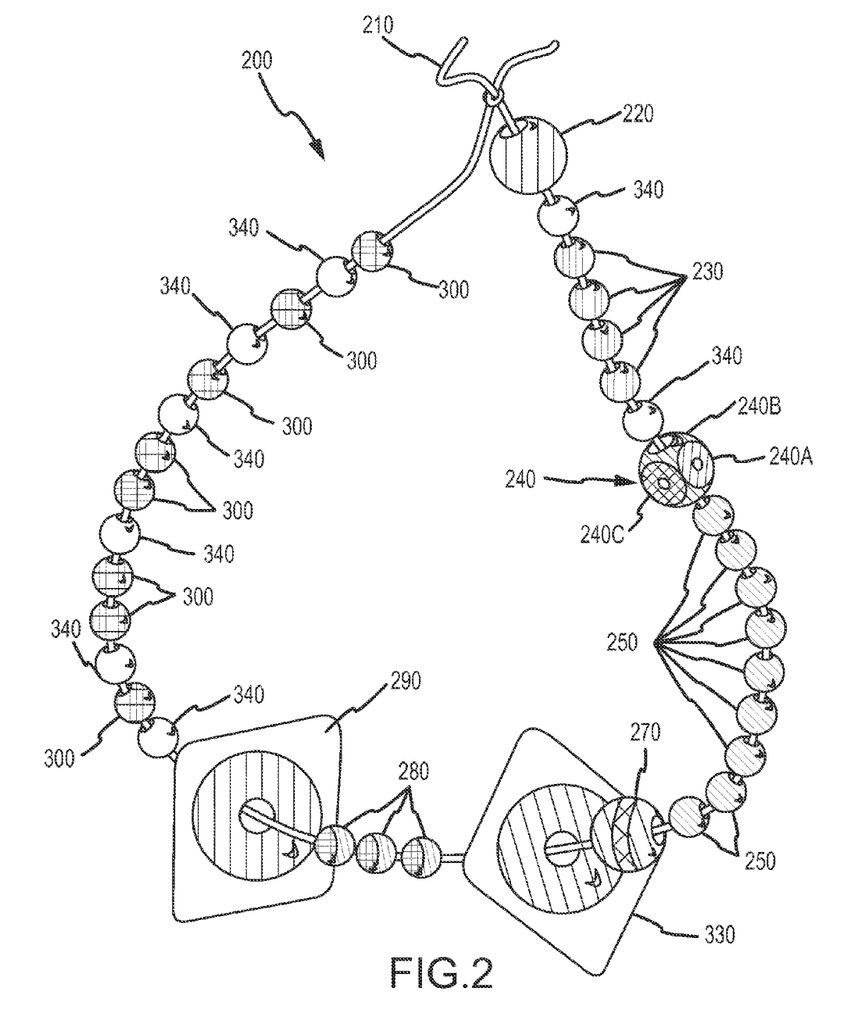
FIG. 2 shows one embodiment of an apparatus for providing visual indications relating to various phases of a woman's menstrual cycle in accordance with the present invention.

One embodiment of an apparatus 200 that may be utilized in conjunction with the method (10) to provide the visual indications is illustrated in FIG. 2. In FIG. 2, the apparatus 200 is shown with the various different types of beads 220-340 as positioned on a string 210 at the completion of the woman's menstrual cycle to provide the desired visual indications throughout the progression of the woman's menstrual cycle. In this regard, each bead 220-340 may include a hole for receiving an end of the string 210 there through. As may be appreciated, the beads 220-340 may be configured differently than depicted in FIG. 2, and the string 210 may in general be any similarly configured item such as, for example, wire, fishing line, cord, rope or the like. Further, FIG. 2 illustrates placement of the beads 220-340 for a typical 28 day menstrual cycle. The total number of beads and the number of beads used for particular phases can vary depending upon a particular woman's menstrual cycle, and the method (10) and apparatus 200 are entirely appropriate for use by a woman with different duration menstrual cycles.

The method begins with the step (20) of placing a first type of bead on the string to indicate start of the menses phase of the woman's menstrual cycle. In this regard, the step (20) of placing a first type of bead on the string may be performed on the first day the woman experiences bright red menstrual bleeding. The first type of bead (the "Day One" bead) may, for example, be a large red bead 220 such as shown in FIG. 2.

After placing the first type of bead on the string, in step (30) additional beads are placed on the string to indicate each additional day of menstrual bleeding during the menses phase. In this regard, a second type of bead may be used to differentiate the first day of the menses phase from subsequent days of the menses phase. For example, as shown in FIG. 2, small red beads 230 may be used. Though the number of second type beads placed on the string varies depending on the duration of the woman's menses phase, generally three to six second type beads are placed on the string and, in a woman with regular menstrual cycles typically four second type beads are placed on the string to indicate four additional days of the menses phase.

After the menses phase concludes (typically though not always on the sixth day after the start of the menses phase), in step (40) a third type of bead is placed on the string to indicate the day the menses phase concludes and the woman's menstrual cycle crosses into the fertile phase of the woman's menstrual cycle. As is illustrated in FIG. 2, the third type of bead (the "Crossroads" or "Cross-over" bead) may be a large tri-color bead 240. The tri-color bead 240 includes three differently colored portions, namely a red portion 240A, a green portion 240B and a yellow portion 240C, and three corresponding holes for placement of the tri-color bead 240 in one of three different orientations on the string 210. The tri-color bead 240 may be oriented on the string 210 based, for example, on observations made of the woman's cervical mucus made in step (60) described below. In this regard, if the woman is observed as having continued menstrual bleeding, the large tri-color bead 240 may be placed on the string 210 using the hole through the red portion of the bead 240 to provide an indication of continued menstrual bleeding. If the woman's cervical mucus is observed as being dry or absent, the large tri-color bead 240 may be placed on the string 210 using the hole through the yellow portion of the bead 240 to indicate current infertility. If the woman's cervical mucus is observed as being sticky or egg-white, the large tri-color bead 240 may be placed on the string 210 using the hole through the green portion of the bead 240 to provide an indication that the woman has entered the fertile phase of her menstrual cycle.

After the Crossroads bead is placed on the string, in step (50) additional beads are placed on the string to indicate each additional day of the fertile phase. In this regard, a fourth type of bead may be used to differentiate the additional days of the fertile phase from the first day of the fertile phase when the Crossroads bead is placed on the string. For example, as shown in FIG. 2, small green beads 250 may be placed on the string 210 for additional days of the fertile phase.

During at least the fertile phase (and possibly also during the menses and infertile phases or portions thereof adjacent to the fertile phase), in step (60) the woman's cervical mucus is observed to determine the day when the woman's cervical mucus begins drying up. In this regard, cervical mucus may generally be characterized as being within one of three categories: (1) dry; (2) sticky; or (3) or egg-white. Cervical mucus is characterized as being dry when cervical mucus is absent. Cervical mucus is considered to be dry when mucus cannot be seen or touched and the woman feels no wetness at her vaginal opening. Cervical mucus is characterized as sticky when the woman feels no wetness at her vaginal opening but can see opaque, cloudy, non-egg white mucus and can touch mucus that is pasty, tacky, mounds up and does not stretch. Cervical mucus is characterized as being egg-white when the woman feels wetness at her vaginal opening, sees mucus of the color of uncooked raw egg-whites and can touch mucus that feels wet and slippery and is stretchy. During the fertile phase, the woman's cervical mucus typically progresses from sticky, to an egg-white peak, back to sticky, and then dry. Observing this progression allows the day following the egg-white peak when the cervical mucus begins drying up to be identified.

In step (70), a fifth type of bead is placed on the string to indicate the day the woman's cervical mucus begins drying up (the "first drying up day"). In this regard, the fifth type of bead (the "first drying up bead") may be a large green bead with a yellow stripe 270 as is illustrated in FIG. 2.

Following placement of the first drying up bead on the string in step (70), step (80) is undertaken. In step (80), additional beads are placed on the string to indicate each additional day that the woman's cervical mucus is drying up. In this regard, a sixth type of bead may be used to differentiate the additional days during which cervical mucus is drying following the first drying up day indicated by the first drying up bead. For example, as shown in FIG. 2, small half green/half yellow colored beads 280 may be placed on the string 210 to indicate the additional days of cervical mucus drying. Typically, as is illustrated in FIG. 2, three half green/half yellow beads 280 are placed on the string 210 to mark three additional days of cervical mucus drying following the large green with yellow stripe bead 270 marking the first drying up day.

After the drying up beads are placed on the string in steps (70) and (80), step (90) is undertaken. In step (90) a seventh type of bead is placed on the string to indicate the first day of the infertile phase of the woman's menstrual cycle. The seventh type of bead may comprise a yellow diamond bead 290 such as shown in FIG. 2.

After step (90), step (100) is undertaken. In step (100) additional beads are placed on the string to indicate each additional day of the infertile phase of the woman's menstrual cycle. In this regard, an eighth type of bead may be used to differentiate the additional days of the infertile phase from the first day of the infertile phase indicated by the seventh type of bead. For example, as shown in FIG. 2, small yellow colored beads 300 may be placed on the string 210 to indicate the additional days of the infertile phase. Yellow beads 300 are placed on the string 210 until the woman's menstrual cycle begins again with bright red menstrual bleeding.

Once the woman's menstrual cycle begins again, the number, order and types of beads on the string may be recorded on a paper chart or the like in step (110) for future reference. Thereafter, the beads may be removed from the string and the method (10) may be started over to provide visual indications relating to the phases of the next menstrual cycle.

Figure 3:
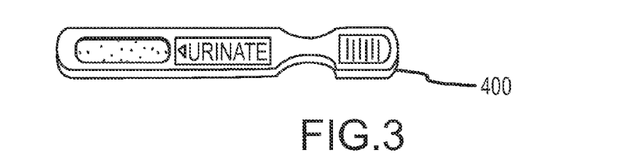
FIG. 3 shows one embodiment of an ovulation prediction kit that may be used in connection with the present invention.

During the method (10), several additional steps may be performed. During the fertile phase, step (120) may be undertaken. In step (120), a urine ovulation prediction kit 400 such as shown in FIG. 3 is utilized to determine the day when the level of luteinizing hormone (LH) released by the woman's pituitary gland surges. The LH surge generally correlates with the cervical mucus peak. Thereafter, in step (130) a ninth type of the bead is placed on the string to indicate the day when LH level surges. The ninth type of bead is placed on the string during the fertile phase in addition to the fourth, fifth, or sixth type of bead placed on the string in steps (50), (70), or (80). The ninth type of bead may comprise a green diamond 330 such as is illustrated in FIG. 2.

Another additional step that may be undertaken as part of the method (10) is step (140). Step (140) may be performed throughout the menses, fertile and infertile phases of the woman's menstrual cycle. In step (140) a tenth type of bead is placed on the string for each day that the woman engages in a coital act. A tenth type of bead is placed on the string in addition to (and preferably behind) the other appropriate type of bead that is placed on the string for the particular day. Placing such beads on the string serves as a means of charting to assist the woman and her partner in comprehending appropriate times to engage or not engage in coital acts depending upon their desire to become or not become pregnant. The tenth type of bead may comprise a gold colored bead 340 such as shown in FIG. 2.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. An apparatus for providing daily visual indications relating to various phases of a woman's menstrual cycle, said apparatus comprising:

a string;

a first bead of a first color positioned on the string to indicate the first day of a menses phase of the woman's menstrual cycle, the first bead being removed from the string at the end of the woman's menstrual cycle;

a plurality of second beads positioned on the string to indicate each additional day of the menses phase, the second beads being of the first color and different in size than the first bead and being removed from the string at the end of the woman's menstrual cycle;

a third bead positioned on the string to indicate the day the woman's menses phase crosses over to a fertile phase of the woman's menstrual cycle, the third bead being of the first color, a second color, and a third color and different in size than the second beads and being removed from the string at the end of the woman's menstrual cycle;

a plurality of fourth beads positioned on the string to indicate each additional day of the fertile phase, the fourth beads being of the second color and being removed from the string at the end of the woman's menstrual cycle;

a fifth bead positioned on the string to indicate the day the woman's cervical mucus begins drying up, the fifth bead being of the second and third colors and being removed from the string at the end of the woman's menstrual cycle;

a plurality of sixth beads positioned on the string to indicate each additional day the woman's cervical mucus is drying up, the sixth beads being of the second and third colors and different in size than the fifth bead and being removed from the string at the end of the woman's menstrual cycle;

a seventh bead positioned on the string to indicate the first day of an infertile phase of the woman's menstrual cycle, the seventh bead being of the third color and being removed from the string at the end of the woman's menstrual cycle; and a plurality of eighth beads positioned on the string to indicate each additional day of the infertile phase, the eighth beads being of the third color and shaped different from the seventh bead and being removed from the string at the end of the woman's menstrual cycle.

2. The apparatus of claim 1 wherein there is a total of four of the second beads.

3. The apparatus of claim 1 wherein there is a total of three of the sixth beads.

4. The apparatus of claim 1 further comprising:
an ovulation prediction kit for determining the day during the fertile phase when a level of luteinizing hormone released by the woman's pituitary gland surges; and
a ninth bead positioned on the string to indicate the day when the luteinizing hormone level surges, the ninth bead being of the second color and shaped different from the fourth beads and being removed from the string at the end of the woman's menstrual cycle.

5. The apparatus of claim 4 further comprising:
a plurality of tenth beads positioned on the string to indicate days on which the woman engages in a coital act, the tenth beads being of a fourth color and being removed from the string at the end of the woman's menstrual cycle.

6. The apparatus of claim 5 wherein:
the second beads are smaller in size than the first bead;
the third bead is larger in size than the second beads;
the fifth bead is larger in size than the sixth beads; and
the sixth beads are smaller in size than the fifth bead.

7. The apparatus of claim 4 wherein:
the second beads are smaller in size than the first bead;
the third bead is larger in size than the second beads;
the fifth bead is larger in size than the sixth beads; and
the sixth beads are smaller in size than the fifth bead.

8. The apparatus of claim 1 wherein:
the second beads are smaller in size than the first bead;
the third bead is larger in size than the second beads;
the fifth bead is larger in size than the sixth beads; and
the sixth beads are smaller in size than the fifth bead.

9. An apparatus that provides daily visual indications relating to various phases of a woman's menstrual cycle, said apparatus comprising:
an ovulation prediction kit for determining the day during a fertile phase of the woman's menstrual cycle when a level of luteinizing hormone released by the woman's pituitary gland surges, wherein the surge in the woman's luteinizing hormone level is correlated with the day of a cervical mucus peak in the woman's menstrual cycle;
a string;
a first type of bead positioned on the string to indicate the first day of a menses phase of the woman's menstrual cycle and removed from the string at the end of the woman's menstrual cycle;
a plurality of a second type of beads positioned on the string to indicate each additional day of the menses phase and removed from the string at the end of the woman's menstrual cycle;
a third type of bead positioned on the string to indicate the day the woman's menses phase crosses over to a fertile phase of the woman's menstrual cycle and removed from the string at the end of the woman's menstrual cycle;
a plurality of a fourth type of beads positioned on the string to indicate each additional day of the fertile phase and removed from the string at the end of the woman's menstrual cycle;
a fifth type of bead positioned on the string to indicate the day the woman's cervical mucus begins drying up and removed from the string at the end of the woman's menstrual cycle;
a plurality of a sixth type of beads positioned on the string to indicate each additional day the woman's cervical mucus is drying up and removed from the string at the end of the woman's menstrual cycle;
a seventh type of bead positioned on the string to indicate the first day of an infertile phase of the woman's menstrual cycle and removed from the string at the end of the woman's menstrual cycle;
a plurality of an eighth type of beads positioned on the string to indicate each additional day of the infertile phase and removed from the string at the end of the woman's menstrual cycle; and
a ninth type of bead positioned on the string to visually indicate the day of the cervical mucus peak in the woman's menstrual cycle when the luteinizing hormone level surges based on a result from the ovulation prediction kit and removed from the string at the end of the woman's menstrual cycle;
wherein at least one of said first, second, third, fourth, fifth, sixth, seventh, eighth, and ninth types of beads is of at least two colors and wherein at least two of said first, second, third, fourth, fifth, sixth, seventh, eighth, and ninth types of beads are different from one another in at least one of shape and size.

10. The apparatus of claim 9 wherein there is a total of four of the second type of beads.

11. The apparatus of claim 9 wherein there is a total of three of the sixth type of beads.

12. The apparatus of claim 9 wherein:
the first type of bead is of a first color;
the second type of beads are of the first color and are smaller in size than the first type of bead;
the third type of bead is of the first color, a second color, and a third color and is larger in size than the second type of beads;
the fourth type of beads are of the second color;
the fifth type of bead is of the second color and the third color and is larger in size than the sixth type of beads;
the sixth type of beads are of the second color and the third color and are smaller in size than the fifth type of bead;
the seventh type of bead is of the third color and is shaped differently from the eighth type of beads;
the eighth type of beads are of the third color; and
the ninth type of bead is of the second color and is shaped differently from the fourth type of beads.

13. The apparatus of claim 9 further comprising:
a plurality of a tenth type of beads positioned on the string to indicate days on which the woman engages in a coital act and removed from the string at the end of the woman's menstrual cycle.

14. The apparatus of claim 13 wherein:
the first type of bead is of a first color;
the second type of beads are of the first color and are smaller in size than the first type of bead;

the third type of bead is of the first color, a second color, and a third color and is larger in size than the second type of beads;

the fourth type of beads are of the second color;

the fifth type of bead is of the second color and the third color and is larger in size than the sixth type of beads;

the sixth type of beads are of the second color and the third color and are smaller in size than the fifth type of bead;

the seventh type of bead is of the third color and is shaped differently from the eighth type of beads;

the eighth type of beads are of the third color;

the ninth type of bead is of the second color and is shaped differently from the fourth type of beads; and the tenth type of beads are of a fourth color.

15. An apparatus that provides daily visual indications relating to various phases of a woman's menstrual cycle, said apparatus comprising:

a string;

a plurality of beads, each bead being positioned on the string to indicate different days of the woman's menstrual cycle and removed from the string at the end of the woman's menstrual cycle, the plurality of beads including:

a first type and a second type of the beads associated with a menses phase of the woman's menstrual cycle;

a third type and a fourth type of the beads associated with a fertile phase of the woman's menstrual cycle, wherein one of the third type and the fourth type of the beads is associated with the day the woman's menses phase crosses over to a fertile phase of the woman's menstrual cycle, the one of the third type and the fourth type of beads associated with the day the woman's menses phase crosses over to the fertile phase of the woman's menstrual cycle being orientable in at least three different orientations on the string to indicate a result of an observation of the woman's cervical mucus and comprising a tri-color bead having three holes formed therethrough, wherein:

a first one of the holes includes an opening in a first color portion of the tri-color bead, the first color portion being associated with a continued menstrual bleeding result of the observation;

a second one of the holes includes an opening in a second color portion of the tri-color bead, the second color portion being associated with a dry or absent cervical mucus result of the observation; and a third one of the holes includes an opening in a third color portion of the tri-color bead, the third color portion being associated with a sticky or egg-white cervical mucus result of the observation;

a fifth type and a sixth type of the beads associated with days on which the woman's cervical mucus is drying up; and a seventh type and an eighth type of the beads associated with an infertile phase of the woman's menstrual cycle;

wherein each of said first, second, third, fourth, fifth, sixth, seventh, and eighth types of beads are different in appearance from one another in at least one of color, shape, and size.

16. The apparatus of claim 15 further comprising:

an ovulation prediction kit for determining the day during a fertile phase of the woman's menstrual cycle when a level of luteinizing hormone released by the woman's pituitary gland surges; and wherein the plurality of beads further includes:

a type of bead associated with the day when the luteinizing hormone level surges.

17. The apparatus of claim 15 wherein the plurality of beads further includes:

a type of bead associated with days on which the woman engages in a coital act.

18. The apparatus of claim 15 wherein:

the two types of beads associated with the menses phase of the woman's menstrual cycle comprise a larger bead of a first color and a plurality of smaller beads of the first color;

one of the types of beads associated with the fertile phase of the woman's menstrual cycle comprises a plurality of beads of a second color;

the two types of beads associated with days on which the woman's cervical mucus is drying up comprise a larger bead of the second color and a third color and a plurality of smaller beads of the second color and the third color; and the two types of beads associated with an infertile phase of the woman's menstrual cycle comprise a plurality of beads of the third color and a differently shaped bead of the third color.

* * * * *

UNITED STATES PATENT AND TRADEMARK OFFICE
CERTIFICATE OF CORRECTION

PATENT NO.       : 7,588,544 B2                          Page 1 of 1
APPLICATION NO.  : 10/783647
DATED            : September 15, 2009
INVENTOR(S)      : George Mulcaire-Jones It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this

Twenty-first Day of September, 2010

David J. Kappos
*Director of the United States Patent and Trademark Office*